United States Patent [19]

Harandi et al.

[11] Patent Number: 5,019,353
[45] Date of Patent: May 28, 1991

[54] REACTOR SYSTEM FOR CONVERSION OF ALKANES TO ALKENES IN AN EXTERNAL FCC CATALYST COOLER

[75] Inventors: Mohsen N. Harandi, Lawrenceville; Hartley Owen, Belle Mead, both of N.J.

[73] Assignee: Mobil Oil Corporation, Fairfax, Va.

[21] Appl. No.: 324,783

[22] Filed: Mar. 17, 1989

Related U.S. Application Data

[63] Continuation-in-part of Ser. No. 144,990, Jan. 19, 1988, Pat. No. 4,840,928.

[51] Int. Cl.$^5$ .................... F27B 15/00; F27B 15/16; B01J 8/18
[52] U.S. Cl. .................... 422/144; 422/145; 422/146
[58] Field of Search ............... 422/143, 144, 145, 146

[56] References Cited

U.S. PATENT DOCUMENTS

| | | | |
|---|---|---|---|
| 2,424,147 | 7/1947 | Campbell | 422/145 X |
| 3,821,103 | 6/1974 | Owen et al. | 422/144 X |
| 3,856,659 | 12/1974 | Owen | 422/144 X |

Primary Examiner—Robert J. Warden
Assistant Examiner—Amalia L. Santiago
Attorney, Agent, or Firm—Alexander J. McKillop; Charles J. Speciale; L. G. Wise

[57] ABSTRACT

A fluid catalytic cracking reactor system useful for regenerating and recycling hot cracking catalyst while utilizing thermal energy therefrom comprising: pressurized regenerator vessel for regenerating a coke-contaminated fluid cracking catalyst in a regeneration zone, maintaining oxidation regeneration temperature and receiving sufficient oxygen-containing regeneration gas to maintain a dense fluid bed of regenerator catalyst so as to regenerate the catalyst before recycling it to a fluid cracker; first valved conduit for withdrawing a controlled stream of regenerator catalyst from the regenerator vessel; dehydrogenation reactor in valved communication with the regenerator vessel, the dehydrogenation reactor having a dehydrogenation zone maintained at temperature below that in the regeneration zone, with the dehydrogenation reactor being located externally relative to the cracker and regenerator vessel; fluid handling for introducing a lower alkane feedstream into the dehydrogenation zone in an amount sufficient to maintain hot withdrawn catalyst in a state of fluidization in the dehydrogenation reactor while cracking catalyst is being cooled; second valved conduit for transporting cooled catalyst from the dehydrogenation zone to the regeneration vessel or fluid cracker; and a conduit for withdrawing an effluent stream from the dehydrogenation reactor.

Lower alkane conversion is an endothermic reaction, wherein the catalyst is autogeneously cooled before it is recirculated to the FCC regenerator.

7 Claims, 2 Drawing Sheets

REACTOR SYSTEM FOR CONVERSION OF ALKANES TO ALKENES IN AN EXTERNAL FCC CATALYST COOLER

REFERENCE TO COPENDING APPLICATION

This application is a continuation-in-part of copending U.S. patent application Ser. No. 144,990, filed 19 Jan. 1988, now U.S. Pat. No. 4,840,928 issued June 20, 1989, incorporated herein by reference.

BACKGROUND OF THE INVENTION

Conventionally, catalyst from a fluid catalyst cracking (FCC) unit is regenerated because it is contaminated with a carbonaceous deposit, coke, in an operating fluid bed catalytic cracker. An FCC regenerator operates at very high oxidative temperature due to the high heat release of burning coke. The capacity of many FCC units is limited by the regenerator operating temperature, which approaches the limit beyond which the regenerator may not be operable because of its metallurgy. Hot regenerated catalyst is conventionally cooled in a catalyst cooler ("catcooler") by generating steam. The catcooler may be either internal or external to the regenerator vessel.

Heat generated in a conventional regenerator is typically removed by internal coils (regen coils) functioning as an internal catcooler, or, by an ECC (external catcooler) in which hot catalyst is contacted with cooling fluid in heat exchanger tubes. Prolonged operation of a regenerator at a temperature at which the catalyst's efficiency is not deleteriously affected bestows upon the operation of any catcooler, a criticality which demands near-absolute reliability of operation. Because such reliability has been so well established by tubes carrying cooling fluid, a heat exchanger is a logical choice, and has been for many years. Because of the relatively high temperature, in the range from about 621° C. to 732° C. (1150°-1350° F.), at which a large volume of regenerated catalyst must be returned to the cracker of an operating refinery, it is evident that the drop in catalyst temperature due to cooling cannot be large, but the amount of heat to be removed is very large. This makes the generation of steam a logical choice.

Prior art FCC regenerators with catcoolers are disclosed in U.S. Pat. Nos. 2,377,935; 2,386,491; 2,662,050; 2,492,948; and 4,374,750. All these prior art catcoolers remove heat by indirect heat exchange, typically a shell and tube exchanger. None removes heat by direct heat exchange, for example, by continuously diluting hot regenerated catalyst with cold catalyst, or by blowing cold air through the hot catalyst; more particularly, none removes heat by functioning as a reactor which supplies heat to an endothermic reaction.

U.S. Pat. No. 4,422,925 discloses the step-wise introduction of ethane, propane, butane, recycle naphtha, naphtha feed, raffinate naphtha, and fractionator bottoms recycle in the riser reactors of a FCC unit. In the riser reactors, the lower alkanes are contacted, in a transport zone, with hot regenerated catalyst which would dehydrogenate the alkanes, progressively decreasing the temperature of the suspension of catalyst and hydrocarbons as they progress upwards through the risers. The mixture of catalyst and reaction products is then contacted with a hydrocarbon feedstock suitable for catalytic cracking, such as virgin naphtha, virgin gas oil, light cycle gas oil, or heavy gas oil.

The control of the catalyst temperature in the risers as well as the benefits of dehydrogenation occurring in the risers were both lost when the products from the risers were mixed with the products of the main cracker. Most important is that operation of the reference FCC unit as a combination dehydrogenator and cat cracker failed to provide control of the olefins generated, which control is essential if recovery and subsequent utilization of the olefins is a goal of the process.

The concept of cooling hot regenerated catalyst by using an endothermic reaction, specifically the catalytic dehydrogenation of butane with chromic oxide supported on alumina or magnesia, was disclosed in U.S. Pat. No. 2,397,352 (Hemminger). Though unrelated to operation of a FCC unit, regeneration of the catalyst was required before it was returned to the dehydrogenation reactor. Hemminger provided a catalyst heating chamber for supplying heat to the dehydrogenation reaction to compensate for that lost in the dehydrogenation reaction, and to preheat the butane to raise its temperature to reaction temperatures. Since the disclosure of this old process, the use of large pore zeolites for cracking catalysts was discovered, as was the effectiveness of certain large and intermediate pore zeolites for the conversion of alkanes to olefins. Our process achieves at least 50%, and preferably 70% conversion of propane, and for the first time, makes the process practical in a refinery environment. Though conceptually feasible, the '352 system required pressurizing catalyst powder which was to be recirculated. The result was that the catalyst did not recirculate.

At the present time, there exists a profusion of schemes for dehydrogenating propane, eventually, for the most part, converting it to gasoline or other products far more valuable than propane. For example, U.S Pat. No. 4,293,722 to Ward et al, teaches one such process. These schemes are unequivocally based on the catalytic effect of particular catalysts and rely on reactions which occur at substantially lower temperatures than those used in our process.

This invention relates to an improvement in cooling regen catalyst, which improvement involves novel apparatus and operating techniques for fluid bed FCC catalyst in an ECC under conditions such that the catalyst is cooled while it performs its alkane dehydrogenating function and thereafter may be returned from the ECC to the regenerator.

SUMMARY OF THE INVENTION

It has been discovered that alkanes, preferably $C_3$–$C_4$ lower alkanes, may be converted to olefins in a 'third bed' ECC in which hot catalyst from an FCC regenerator thermally cracks and dehydrogenates the alkanes, and because this is an endothermic reaction, the catalyst is autogeneously cooled before it is recirculated to the FCC regenerator.

It is, therefore, a general object of this invention to provide a reactor system for using heat generated in a regenerator of a FCC cracker. The preferred reactor system for regenerating a coke-contaminated fluid cracking catalyst comprises:

a regeneration vessel having means for maintaining a regeneration zone at a pressure in the range from above 20 psig to about 50 psig and a temperature in the range from about 650° C. to 815° C.;

means for injecting oxygen-containing regeneration gas into said regeneration zone to maintain a dense fluid bed of regenerator catalyst to oxidatively regenerate the catalyst before return to a fluid cracker;

means for withdrawing a controlled stream of said regenerator catalyst and introducing said withdrawn catalyst into a catalyst cooler vessel having a dehydrogenation zone at reaction temperature below said regeneration zone temperature, said catalyst cooler being located separately and external from said cracker and regenerator vessel, the amount of said catalyst stream being sufficient to supply the endothermic heat of reaction for dehydrogenation of alkanes in said dehydrogenation zone;

means for introducing a feedstream of alkanes into said dehydrogenation zone in an amount sufficient to maintain hot withdrawn catalyst in a state of fluidization in said catalyst cooler, said state of fluidization. existing in a sub-transport regime operating at a weight hourly space velocity WHSV of said lower alkanes not to exceed 5 $hr^{-1}$ while maintained at a temperature high enough to convert at least 50% of said alkanes, and concurrently to cool said catalyst;

solids handling means means for transporting cooled catalyst directly from said dehydrogenation zone at dehydrogenation temperature to said regeneration zone, and mixing hot catalyst therein with said cooled catalyst; and means for withdrawing dehydrogenation product in an effluent stream from said catalyst cooler vessel.

BRIEF DESCRIPTION OF THE DRAWING

These and other objects and advantages of the invention will appear more fully from the following description, made in connection with the accompanying drawings of preferred embodiments of the invention, wherein like reference characters refer to the same or similar parts throughout the views and in which.

DETAILED DESCRIPTION OF PREFERRED EMBODIMENTS

Figure 1:
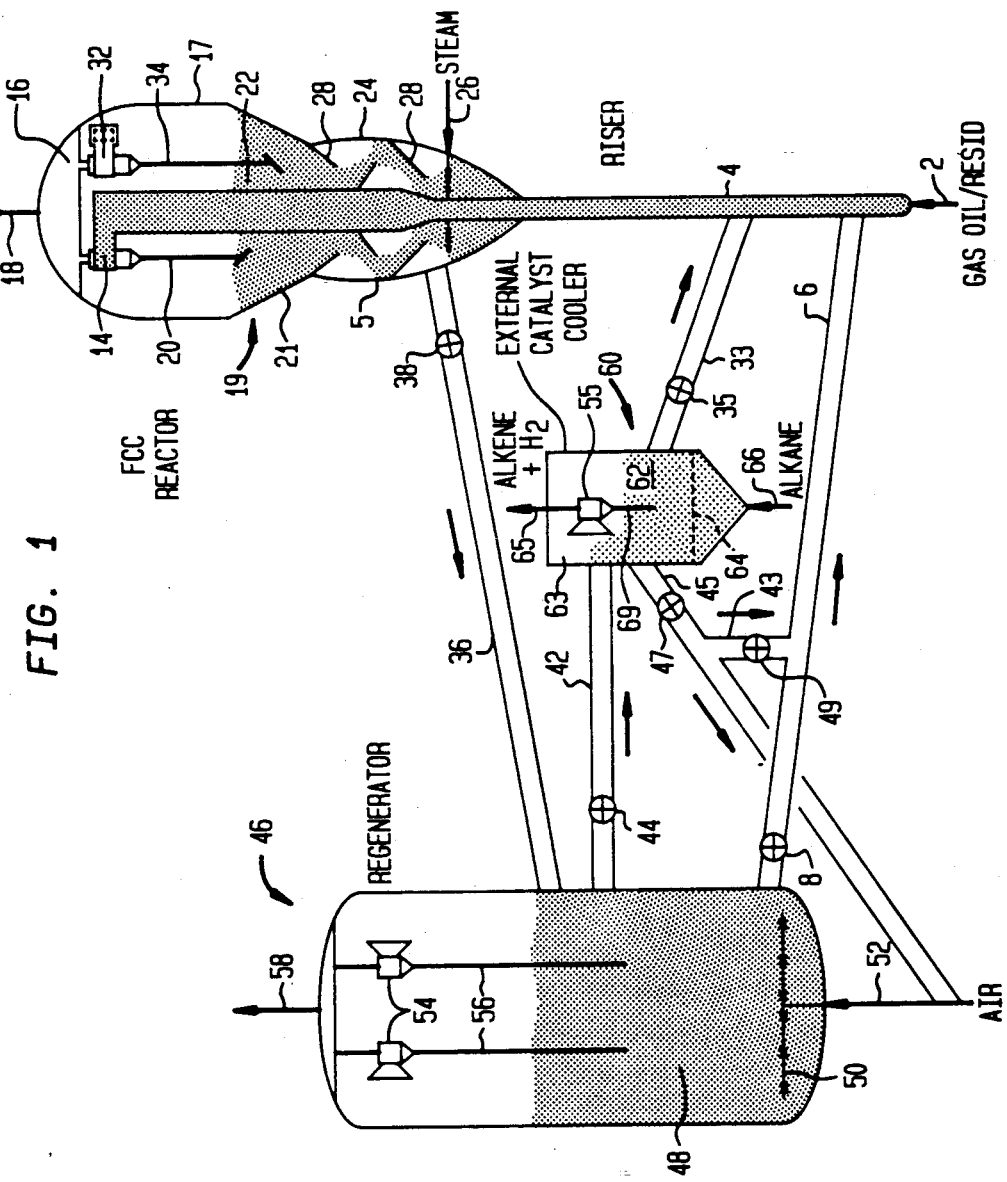
FIG. 1 schematically illustrates a fluidized catalytic cracking unit in which the operation of a regenerator is coupled with that of a fluid bed thermal catalytic cracker and alkane dehydrogenation reactor which also functions as an external catalyst cooler (ECC). This ECC being an endothermic reactor, provides a similar cooling function as that provided by a conventional shell-and-tube heat exchanger used as an ECC.

In this invention the regenerated catalyst is cooled in an external catalyst cooler (ECC), which also functions as a dehydrogenation reactor for converting alkanes to alkenes. More specifically, this invention relates to coupling the dehydrogenation of a lower $C_2$-$C_6$ alkane, preferably propane ($C_{3p}$) and butane ($C_{4b}$), and most preferably propane, with the operation of a FCC cracker and its regenerator, in the specific instance where the temperature of operation of the regenerator permits using the FCC catalyst as an effective propane dehydrogenation agent.

As will hereinafter be described, the dehydrogenation reaction occurs in the ECC due to thermal catalytic cracking which is partly a pyrrolytic thermal reaction, referred to herein as thermal dehydrogenation, and partly a dehydrogenation catalytic effect of the FCC catalyst. Since it is the FCC catalyst which is responsible for the dehydrogenation, we refer to it as "dehydrogenation catalyst" or "ECC catalyst" when it is in the ECC, just as we refer to the catalyst being regenerated as "regen catalyst", though it is only being regenerated. The thermal dehydrogenation of normally liquid hydrocarbons at a temperature in the range from 538° C. to 750° C. (1000–1382° F.) by pyrolysis in the presence of steam, is disclosed in U.S. Pat. Nos. 3,835,029 and 4,172,816, inter alia, but there is no suggestion that such a reaction may be used as the basis for direct heat exchange, to cool regen catalyst in an ECC for a FCC unit.

In a preferred embodiment, this invention is carried out with a cracker catalyst consisting essentially of large pore crystalline silicate zeolite, generally in a suitable matrix component. The particular cracker catalyst used is not critical to initiate the dehydrogenation reaction since part of the reaction is due to thermal cracking. The product yield and selectivity, however, is affected by the catalyst type and its metal content. Most preferred is a rare earth promoted FCC catalyst in which additional metal promoters, particularly nickel and vanadium, are laid down by the vacuum gas oil (VGO) or resid feed to the FCC riser, and the metals are oxidized in the regenerator. In addition, the FCC catalyst may contain a small amount of Pt, usually less than 300 ppm, to boost the oxidation of CO to $CO_2$ in the regenerator. Since control of the distribution of products from the FCC is much more important than control of the distribution of products obtained by dehydrogenation, the preferred catalyst for our process is the FCC catalyst of choice.

Conventional non-zeolitic FCC catalysts may be used which are generally amorphous silica-alumina and crystalline silica-alumina. Other non-zeolitic materials said to be useful as FCC catalysts are the crystalline silicoaluminophosphates of U.S. Pat. No. 4,440,871 and the crystalline metal aluminophosphates of U.S. Pat. No. 4,567,029. However, the most widely used FCC catalysts are large pore crystalline silicate zeolites known to possess some catalytic activity with particular respect to converting lower alkanes to alkenes, and specifically propane to propylene, at a temperature and pressure lower than those at which the regenerator of the FCC unit operates.

Such zeolites typically possess an average (major) pore dimension of about 7.0 angstroms and above. Representative crystalline silcate zeolite cracking catalysts of this type include zeolite X (U.S. Pat. No. 2,882,244), zeolite Y (U.S. Pat. No. 3,130,007), zeolite ZK-5 (U.S. Pat. No. 3,247,195), zeolite ZK-4 (U.S. Pat. No. 3,314,752), merely to name a few as well as naturally occurring zeolites, such as chabazite, faujasite, modernite, and the like. Also useful are the silicon-substituted zeolites described in U.S. Pat. No. 4,503,023. Zeolite Beta is yet another crystalline silicate which can constitute a component of the mixed catlayst system herein.

Most preferred is a large pore crystalline silicate zeolite promoted with a catalytic amount of metal or metal oxide of an element selected from Groups V and VIII of the Periodic Table, sufficient to enhance the dehydrogenation activity of the FCC catalyst. Though typically, only one of the aforementioned catalysts is used in a cracker, combinations of two or more may also be used. In addition to the foregoing catalysts, a mixed catalyst system in which a catalyst requiring frequent regeneration, such as zeolite Y, may be employed in combination with a shape selective medium pore crystalline silicate zeolite catalyst requiring comparatively infrequent regeneration such as ZSM-5.

The term "catalyst" as used herein shall be understood to apply not only to a catalytically active material but to one which is composited with a suitable matrix component which may or may not itself be catalytically active. By "cracker or cracking catalyst" we refer to any catalyst used in a fluid cracker which catalyst has some propane-dehydrogenation activity under the pressure and temperature conditions specified for operation of the ECC.

The FCC unit is preferably operated under fluidized flow conditions, at a temperature in the range from about 1000° F. to about 1350° F., with a catalyst to charge stock ratio of from about 4:1 to about 20:1, and a contact time of from about 1 to about 20 sec. Generally, it is preferred to crack the charge stock in an upflowing riser conversion zone discharging into cyclonic separation means in an upper portion of an enlarged vessel in which the products of cracking are separated from catalyst.

Preferred charge stocks to the cracker comprise petroleum fractions having an initial boiling point of at least 500° F. (260° C.), a 50% point at least 750° F. (399° C.), and an end point of at least 1100° F. (593° C.). Such fractions include gas oils, thermal oils, residual oils, cycle stocks, whole top crudes, tar sand oils, shale oils, synthetic fuels, heavy hydrocarbon fractions derived from the destructive dehydrogenation of coal, tar, pitches, asphalts, hydrotreated feedstocks derived from any of the foregoing, and the like. As will be recognized, the distillation of higher boiling point fractions, above about 750° F. (399° C.) must be carried out under vacuum to avoid thermal cracking. The boiling temperatures utilized herein are expressed, for convenience, in terms of the boiling point corrected to atmospheric pressure.

The separated catalyst is collected in the lower portion of the vessel which is in open communication with the upper end of a lower extending stripping zone wherein the catalyst is stripped with countercurrent upwardly flowing stripping gas, such as steam. The stripped products and products of conversion separate from the catalyst and are discharged from the riser conversion zone, and are combined with the cyclonically separated hydrocarbon vapors and passed to one or more downstream zones.

The stripped catlayst is transferred to a regenerator for removal of deposited carbonaceous material by burning, thereby heating the catalyst to a temperature in the range from about 1250° F. (675° C.) to about 1500° F. (815° C.).

The foregoing steps in the operation of a FCC unit are conventional, being recited hereinabove only to point out that the conditions at which the steps are practiced, are dictated by the charge stock and the product mix desired, which in turn dictates the operation of the regenerator.

Referring now to FIG. 1, there is schematically illustrated a flowsheet of equipment operatively connected by fluid handling means and solids handling means in which a charge stock (feed) 2, such as gas oil is introduced, after it is preheated, into riser 4, near the bottom. Thus the gas oil is mixed with hot regen catalyst, such as zeolite Y, introduced through a valved conduit means such as standpipe 6 provided with a flow control valve 8. Because the temperature of the hot regenerated catalyst is in the range from about 1200° F. (675° C.) to about 1350° F. (730° C.), a suspension of hydrocarbon vapors is quickly formed, and flows upward through the riser 4.

The riser 4 is flared gently outward into a region 5 through which catalyst and entrained hydrocarbons are flowed, being afforded, in this region 5, the contact time preselected to provide desired cracked products. Catalyst particles and the gasiform products of conversion continue past region 5 and are discharged from the top of the riser into one or more cyclone separators 14 housed in the upper portion 17 of the vessel, indicated generally by reference numeral 19. Riser 4 terminates in a 'bird cage' discharge device, or an open end "T" connection may be fastened to the riser discharge which is not typically directly connected to the cyclonic catalyst separation means.

The effluent from riser 4 comprises catalyst particles and hydrocarbon vapors which are led into the cyclonic separators 14 which effect separation of catalyst from hydrocarbon vapors. Such vapors pass into a plenum chamber 16 and thence are removed through conduit 18 for recovery and further processing. Hydrocarbon vapors from cyclone 14 are discharged to a plenum chamber 16 from which they flow through conduit 18 for further processing and recovery, typically to a fractionator column where the products of cracking are separated into preselected fractions.

Catalyst separated from the vapors descends through dipleg 20 to a fluid bed 22 of catalyst maintained in the lower portion 21 of the vessel 19. The bed 22 lies above, and in open communication with a stripping zone 24 into which the catalyst progresses, generally downward, and countercurrent to upflowing steam introduced through conduit 26. Baffles 28 are provided in the stripping zone to improve stripping efficiency.

Spent catalyst, separated from the hydrocarbon vapors in the cyclones, is maintained in the stripping zone 24 for a period of time sufficient to effect a higher temperature desorption of feed-deposited compounds which are then carried overhead by the steam. The stripping zone is maintained at a temperature of about 1250° F. or even higher if hot regenerated catalyst is introduced into the stripping zone by means not shown, as is sometimes done. The steam and desorbed hydrocarbons pass through one or more cyclones 32 which return catalyst fines through dipleg 34 to the bed 22.

Stripped catalyst flows though conduit 36, provided with flow control valve 38, to regenerator vessel 46 including a regeneration zone containing a dense fluid bed 48 of catalyst into the lower portion of which bed, regeneration gas, typically air, is introduced by distributor 50 supplied by conduit 52. Cyclone separators 54 provided with diplegs 56 separate entrained catalyst particles from flue gas and return the separated catalyst to the fluid bed 48. Flue gases pass from the cyclones into a plenum chamber and are removed therefrom by conduit 58. Hot regenerated catalyst is returned to the bottom of riser 4 by conduit 6, to continue the process with another conversion cycle, all of which is conventionally practiced.

In the improvement according to this invention, solids handling means are provided whereby hot regen catalyst flows though conduit 42, provided with flow control valve 44, to ECC 60 containing a fluid bed 62 of ECC catalyst. As schematically illustrated, the ECC is coupled to the regenerator through the catalyst transfer lines but is physically located externally relative to both the regenerator and the cracker. Into the lower portion of the ECC bed is introduced a feedstream of lower alkanes to be dehydrogenated. Most preferred is a feedstream in which propane is the major constituent relative to the total weight of other hydrocarbon components. The propane is supplied by fluid handling means including distributor 64 fed through conduit 66, typically in conjunction with minor amounts of other lower alkanes and even smaller amounts of olefins scavenged from various waste refinery streams. The hot stream of regen catalyst withdrawn from the regenerator is quickly cooled by direct contact with the relatively cool gases and catalyst in the ECC bed.

The ECC generally operates at relatively low space velocity (WHSV) in the range from 0.01 to 5.0 $hr^{-1}$, preferably from 0.1 to 1.0 $hr^{-1}$, and in a relatively narrow pressure and temperature range from above 20 psig to about 50 psig (239-446 kPa), preferably 25 psig to about 45 psig (273-411 kPa), and from about 1200° to 1500° F. (650-815° C.), preferably up to 1350° F. (732° C.), depending upon the pressure and temperature at which the regenerator is operated.

The amount of heat supplied to the ECC is determined by a controlled amount of catalyst withdrawn from the regenerator. The rate at which the catalyst stream is withdrawn depends upon the temperature at which the regenerator is to be operated, which in turn determines the amount of alkanes which may be dehydrogenated. For a given flow of regenerated catalyst to the ECC at a preselected temperature, and a given rate of lower alkane charged, the temperature of catalyst in the ECC is controlled in the range from about 1100° to 1350° F. (593-732° C.) by the temperature to which the charge is preheated.

Cyclone separators 55 provided with a dipleg 69 separates entrained catalyst particles from ethylene, propylene, hydrogen, butylenes, other hydrocarbon products, and unconverted alkanes, and return the separated catalyst to the fluid bed 62. The products of conversion of the dehydrogenation reaction pass from the cyclones into a plenum chamber 63 and are removed therefrom by effluent line 65. Relatively cool ECC catalyst is returned to the regenerator 46 through conduit 45 provided with a valve 47, by being lifted with air in the airlift conduit 52.

If desired, the regenerator may be partly or completely bypassed by flowing the cooled catalyst from the ECC through conduit 33, provided with valve 35, to the riser 4. For greater flexibility of operation, a portion of the cooled catalyst from the ECC is returned to the regenerator through line 45, and the remainder flowed through line 33 to the riser.

Regenerated catalyst is removed from the regenerator through return conduit 6 controlled by valve 8, for passage to the riser 4 of the cracker, either above or below the point where line 33 communicates with the riser. This bypassing of the regenerator by directly flowing cooled catalyst to the FCC riser is desirable in cases where maximizing catalyst circulation and minimizing thermal cracking because of the relatively low catalyst temperature in the FCC riser, is desired. Again, for additional flexibility of operation, cooled catalyst from the line 45 may be flowed through conduit 43, controlled by valve 49, into the return conduit 6.

Figure 2:
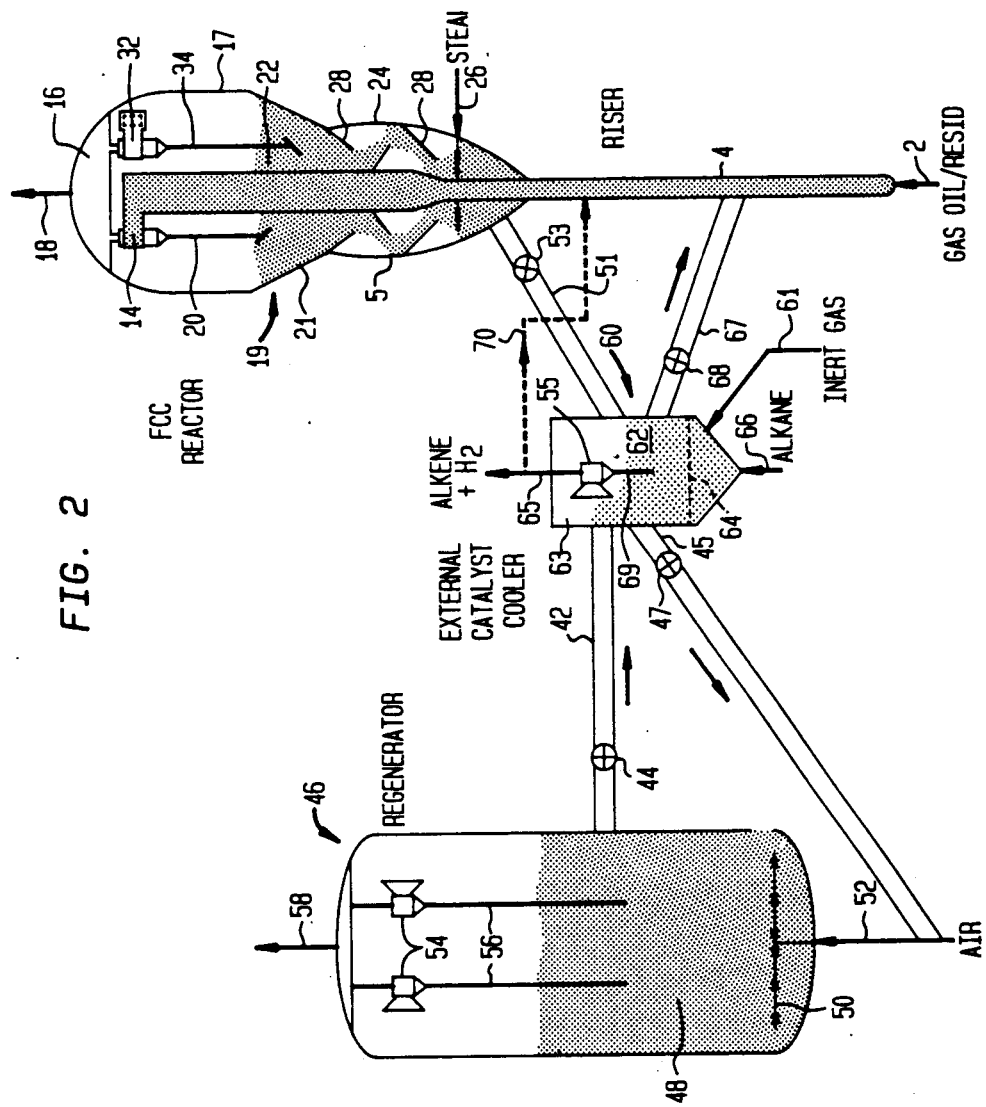
FIG. 2 schematically illustrates the operation of a regenerator from which regen catalyst is cooled in an ECC to which coked up catalayst is flowed from the cracker. A portion of cooled catalyst is flowed from the ECC to a riser of the FCC.

Referring now to FIG. 2 there is schematically illustrated yet another embodiment of the invention which is particularly adapted for the operation of the FCC with resid, but may equally be used for cracking gas oil.

In this embodiment, spent catalyst from dip legs 20 and 34 of the the FCC, is flowed at from bout 1000°-1050° F. (537.8°-565.5° C.) through conduit 51, controlled by valve 53, directly to the ECC 60 so that the alkane feed to the ECC strips hydrocarbons remaining in the pores of the catalyst. The ECC preferably operates at a pressure in the range from 25-45 psig (273-411 kPa) and a temperature in the range from about 1200°-14000° F. (649°-760° C.).

To aid in the stripping, an inert gas stream unreactive with the hydrocarbons under the operating conditions of the ECC, typically steam, optionally in combination with a portion of the alkane feed to be dehydrogenated, may be injected through line 61 into the ECC in an amount sufficient to effect the stripping. A slipstream 70 of effluent from the effluent line 65 may be introduced into the riser 4, if desired. The superficial velocity of alkane in the ECC is preferably in the range from about 0.3 to 5 ft/sec, and that of the steam from 0 to 0.2 ft/sec. It will be found that a lower superficial velocity than 0.3 ft/sec of alkane is not generally economical, and neither is more than 0.2 ft/sec of steam. Cooled catalyst from the ECC is returned through conduit 67, controlled by valve 68, directly to the FCC riser 4. Thus, it will now be evident that the ECC replaces the conventional function of a stripper for the FCC cracker.

The preferred conditions of operation of the ECC are such that about 70% of the propane fed is converted per pass at a space velocity which is no greater than 1 $hr^{-1}$ WHSV. Higher conversions are obtained with butanes, and lower conversions with ethane.

As may be expected in a thermal dehydrogenation reaction, the conversion and selectivity depends mainly upon the specific process conditions of operation of the ECC, and only to a minor extent upon the particular FCC catalyst being used, unless the catalyst is promoted with specific promoters which enhance the dehydrogenation activity of the FCC catalyst. Most preferred promoters for a faujasite catalyst are nickel and vanadium oxides.

Since FCC catalyst captures nickel and vanadium in the FCC feed, dehydrogenation activity of the FCC catalyst is enhanced after it is regenerated. In all instances, the selectivity of conversion from propane to propylene decreases as the conversion increases at a preselected temperature. Also, propane conversion increases as the reaction temperature increases or space velocity decreases. The extent of side reactions such as propane cracking, oligomerization of propylene and ethylene, dehydrogenation of ethane, and isomerization of $C_4$s may be reduced at higher space velocity, but at the expense of propane conversion. In most instances, even when conversion is relatively high, unconverted propane is preferably recycled to the ECC.

The following illustrative example describes a FCC unit processing 2000 barrels/hour of gas oil/resid feed in conjunction with a single stage regenerator. The dense bed of the regenerator vessel has an inventory of 150 short tons (136.07 metric tons) of catalyst. A faujasite FCC catalyst promoted with nickel is used which is to be regenerated at a temperature no higher than 1500° F. (815° C.) to prevent damage to the catalyst. The catalyst is to be conveyed to the riser of the cracker at a temperature of 1250° F. (746° C.).

Accordingly, 10 tons/minute of hot regen catalyst is withdrawn and mixed into the ECC 60 while 1000 lb/min (453.6 kg/min) of a lower alkane feedstream which is preheated to a temperature of 500° F. (260° C.)

by heat exchange (not shown) with products from the overhead effluent of the cracker, are used to maintain the ECC catalyst in a fluidized regime.

The particular level of turbulence is not critical so long as the zone is sub-transport, but it is preferred that the regime be sufficiently turbulent that the fluidization is adequate to effect the heat transfer to cool the hot regen catalyst. The lower alkane feedstream is premixed with the hot regen catalyst so as to function as liftgas lifting the catalyst into the regenerator.

Thus, it will now be evident that the ECC provides a means for adding cooling capacity to an existing regenerator while upgrading a lower alkane stream. The addition of an ECC allows one to feed heavier feedstock to the FCC which will deposit more carbon on the FCC catalyst. The additional heat released by burning off the carbon is compensated for in the ECC while alkanes are converted to more valuable olefins. The valving to vary the flow of catalyst to the ECC, and control the flow from the ECC to the regenerator, permits positive control over operation of the regenerator while it operates "as hot as practical". The process conditions in the ECC make it feasible to control the conversion of at least one alkane in the feedstream so that the effluent from the ECC which comprises alkanes, olefins and hydrogen including minor amounts of aromatics and cycloaliphatics, may be used as feedstock to be upgraded in other sections of the refinery.

In the preferred embodiment as described the regenerator dimensions and temperature are as follows:
Height 90 ft. (27.43 meters) Diameter 25 ft. (7.62 meters).
Hot catalyst removed from regenerator 21,000 lb/min (9,525.6 kg/min), and flowed to ECC.
Temperature of hot regen catalyst 1350° F. (732° C.).

The dimensions of the ECC and conditions of operation with the faujasite catalyst, are as follows:
Height: 60 ft. Diameter: 10 ft. (3.048 m).
Height of fluidized bed: 30 ft. (9.144 m).
Density of fluidized bed: 31 lb/ft$^3$ (496.56 kg/m$^3$).
Average temperature of ECC bed 1250° F. (675° C.).
Superficial velocity of alkane : 1.2 ft/sec (0.365 m/sec).
WHSV: 0.8 hr$^{-1}$.
Temperature of cooled ECC catalyst recycled:(675° C.).

It is advantageous to feed a substantially paraffinic stream consisting essentially of a major amount of propane and a minor amount of propylene and/or ethylene, to an ECC in which a fluid bed of zeolite regen catalyst, promoted with oxides of metals to enhance the dehydrogenation activity of the catalyst. Per pass conversion of at least 50%, and preferably more than 70%, of the propane is obtained, and the catalyst is concurrently cooled autogenously.

It is also desirable to operate with means for diverting a portion of cooled catalyst being returned to the regenerator, so that it may be flow-controlled into the lower portion of a riser of the fluid cracker, preferably near the bottom.

Lower alkane conversion is is an endothermic reaction, wherein the catalyst is cooled before it is recirculated to the FCC regenerator. The external catalyst cooling function eliminates internal regenerator coils for steam regeneration, and allows flexibility in design of its fluid bed for optimum space velocity and control of dehydrogenation temperature.

Maximum conversion of alkanes can be maintained because the FCC regenerator burns coke made during alkane dehydrogenation. The dehydrogenation unit also permits control of the temperature at which the FCC regenerator operates to facilitate processing heavier feedstock in the FCC unit.

We claim:

1. A reactor system comprising:
   a fluid catalytic cracker reactor vessel having a riser connected thereto at a lower portion of said reactor vessel, a regeneration vessel for regenerating a coke-contaminated "spent" fluid cracking catalyst, and an external catalyst cooling vessel,
   said regeneration vessel having means for maintain a regeneration zone at a pressure in the range from about 20 psig to about 50 psig and a temperature in the range from about 650° C. to 815° C.;
   means for injecting oxygen-containing regeneration gas into said regeneration zone to maintain a dense fluid bed of regenerator catalyst to oxidatively regenerate the catalyst;
   a first conduit means including valve means for withdrawing a controlled stream of said spent catalyst from said fluid catalytic cracker reactor vessel and introducing said spent catalyst into said regenerator vessel;
   a second conduit means including valve means extending exteriorly from said said regenerator vessel for withdrawing a controlled stream of regenerated catalyst and introducing said regenerated catalyst directly into said external catalyst cooling vessel wherein a hydrogenation zone is defined at reaction temperature below that in said regeneration zone, said catalyst cooling vessel being located separately from and externally relative to said cracker reactor vessel and said regenerator vessel, the amount of said controlled stream of regenerated catalyst being sufficient to supply the endothermic heat of reaction for dehydrogenation of alkanes in said dehydrogenation zone;
   a third conduit means including valve means for withdrawing a controlled stream of cooled catalyst from said dehydrogenation zone and introducing said cooled catalyst into said riser;
   means for introducing a feedstream of alkanes consisting essentially of a major proportion of propane into said dehydrogenation zone in an amount sufficient to maintain said catalyst therein in a state of fluidization, said state of fluidization existing in a sub-transport regime operating at a weight hourly space velocity WHSV of said lower alkanes not to exceed 5 hr$^{-1}$ while said catalyst is cooled but maintained at a temperature high enough to convert at least 50% of said alkanes;
   a fourth conduit means including valve means for transporting cooled catalyst directly from said dehydrogenation zone at dehydrogenation temperature, into said regeneration vessel, and mixing hot catalyst therein with cooled catalyst; and,
   means for withdrawing olefins generated in said catalyst cooling vessel outside of said system in an effluent stream separate from the effluent from said fluid catalytic cracker to allow recovery and subsequent utilization of said olefins.

2. The reactor system of claim 1 further comprising a fifth conduit means including valve means for withdrawing a controlled stream of said regenerated catalyst from said regenerator vessel and introducing it into said riser in the lower portion of said fluid catalytic cracker vessel.

3. The reactor system of claim 1 further comprising means for diverting a portion of said cooled catalyst being transported form said cooling vessel to said regeneration vessel, and means for flow-controlledly introducing said portion into said riser of said fluid catalytic cracker vessel, in the lower portion thereof.

4. The reactor system of claim 1 in which said cracking catalyst which consists essentially of large pore zeolite catalyst promoted with a catalytic amount of a metal or metal oxide of an element from Group V or VIII.

5. In a fluid catalytic cracking system including regenerator means for regenerating a coke-contaminated fluid cracking catalyst and defining a regeneration zone at a pressure in the range from above 20 psig. to about 50 psig. and a temperature in the range from about 650° C. to 790° C. (about 1200°–1450° F.) while injecting said regenerator zone with enough oxygen-containing regeneration gas to maintain a dense fluid bed of regenerator catalyst so as to regenerate the catalyst before returning it to a fluid cracker reactor vessel having a cracking riser connected thereto, the improvement comprising,
   a) a first valved conduit including control means for withdrawing a controlled stream of said regenerator catalyst from said regeneration means directly into a dehydrogenation zone,
   b) a dehydrogenation reactor vessel in which said dehydrogenation zone is defined and is operated at a temperature below that prevailing in said regeneration means, said dehydrogenation reactor being located externally relative to said cracker reactor vessel and regeneration means,
   c) means for introducing a lower alkane feedstream consisting essentially of a major proportion of propane into said dehydrogenation zone in an amount sufficient to maintain hot withdrawn catalyst in a state of fluidization in said dehydrogenation reactor while said catalyst is being cooled,
   d) a second valve conduit means for transporting cooled catalyst from said dehydrogenation reactor vessel and selectively controlling flow thereof to said regeneration means and to said fluid cracker reactor vessel in the riser thereof, and,
   e) third conduit means for withdrawing olefins generated in said dehydrogenation reactor vessel outside said system in an effluent stream separate from effluent from said fluid cracker reactor vessel to allow recovery and subsequent utilization of said olefins.

6. A fluid catalystic cracking reactor system comprising:
   pressurized regenerator vessel means for regenerating a coke-contaminated fluid cracking catalyst in a regeneration zone including means for maintaining oxidation regeneration temperature and means for injecting said regenerator zone with sufficient oxygen-containing regeneration gas to maintain a dense fluid bed of regenerator catalyst so as to regenerate the catalyst before returning it to a fluid catalytic cracker reactor vessel;
   first valved conduit means including control means for withdrawing a controlled stream of said regenerated catalyst from said regenerator vessel directly into a dehydrogenation zone;
   dehydrogenation reactor means in which said dehydrogenation zone is defined and maintained at a temperature below that in said regeneration zone, said dehydrogenation reactor means being located externally relative to said cracker reactor vessel and regenerator vessel means;
   fluid handling means for introducing a lower alkane feedstream consisting essentially of a major proportion of propane into said dehydrogenation reactor means in an amount sufficient to maintain hot withdrawn catalyst in a state of fluidization in said dehydrogenation reactor means while said catalyst is being cooled;
   second valved conduit means for transporting cooled catalyst from said dehydrogenation zone and selectively controlling flow of said catalyst to said regeneration vessel and to said fluid cracker reactor vessel; and
   third conduit means for withdrawing olefins generated in said dehydrogenation reactor vessel outside of said system, in an effluent stream separate from effluent from said fluid cracker reactor vessel to allow recovery and subsequent utilization of said olefins.

7. A reactor system including a fluid catalytic cracker reactor vessel, a regeneration vessel for regenerating a coke-contaminated "spent" fluid cracking catalyst, and an external catalyst cooling vessel,
   said regeneration vessel having means for defining and maintaining a regeneration zone at a pressure in the range from about 20 psig to about 50 psig and a temperature in the range from about 650° C. to 815° C.;
   means for injecting oxygen-containing regeneration gas into said regeneration vessel to maintain a dense fluid bed of regenerator catalyst to oxidatively regenerate the spent catalyst;
   first conduit means including a valve means for withdrawing a controlled stream of said spent catalyst from said fluid catalytic cracker reactor vessel and introducing said spent catalyst into said external catalyst cooling vessel;
   a second conduit means including a valve means for withdrawing a controlled stream of said regenerated catalyst and introducing said regenerated catalyst directly into said catlayst cooling vessel having a dehydrogenation zone at reaction temperature below that in said regeneration zone, said catalyst cooling vessel being located separately from, and externally relative to said cracker reactor vessel and regenerator vessel, the amount of said controlled stream of regenerated catalyst being sufficient to supply the endothermic heat of reaction for dehydrogenation of alkanes in said dehydrogenation zone;
   a third conduit means including valve means for withdrawing a controlled stream of cooled catalyst from said dehydrogenation zone in said catalyst cooling vessel and introducing said cooled catalyst into said riser;
   means for introducing a feedstream of alkanes consisting essentially of a major proportion of propane into said catalyst cooling vessel and dehydrogenation zone in an amount sufficient to maintain said catalyst therein in a state of fluidization, said state of fluidization existing in a subtransport regime operating at a weight hourly space velocity WHSV of said lower alkanes not to exceed 5 $hr^{-1}$ while said catalyst is cooled but maintained at a temperature high enough to convert at least 50% of said alkanes;

fourth conduit means including valve means for transporting cooled catalyst directly form said dehydrogenation zone in said catalyst cooling vessel at dehydrogenation temperature, to said means for injecting oxygen and into said regeneration zone, and mixing hot catalyst therein with cooled catalyst; and, means for withdrawing olefins generated in said catalyst cooling vessel outside of said system in an effluent stream separate from the effluent from said fluid catalytic cracker to allow recovery and subsequent utilization of said olefins.

* * * * *